US00PP14440P39

(12) United States Plant Patent
Kordes

(10) Patent No.: US PP14,440 P3
(45) Date of Patent: Dec. 30, 2003

(54) HYBRID TEA ROSE PLANT NAMED 'KOROLESOLA'

(50) Latin Name: *Rosa hybrid*
Varietal Denomination: KORolesola

(75) Inventor: Wilhelm Kordes, Rosenstrasse 54, Klein Offenseth-Sparrieshoop (DE), D-25365

(73) Assignee: Wilhelm Kordes, Klein Offenseth-Sparrieshoop (DE)

( * ) Notice: Subject to any disclaimer, the term of this patent is extended or adjusted under 35 U.S.C. 154(b) by 0 days.

(21) Appl. No.: 10/208,710

(22) Filed: Jul. 30, 2002

(65) Prior Publication Data

US 2003/0046738 P1 Mar. 6, 2003

(51) Int. Cl.[7] ..... A01H 5/00

(52) U.S. Cl. ..... Plt./132

(58) Field of Search ..... Plt./132

*Primary Examiner*—Bruce R. Campell
*Assistant Examiner*—A. Para

(57) ABSTRACT

A new and distinct variety of Hybrid Tea rose plant which have attractive creme-pink colored flowers and attractive dark green and glossy foliage. The buds are large and well turbinated. This new variety is having high production of long stems with a long vase life, vigorous, upright growth, and good tolerance to powdery mildew. The variety successfully propagates from softwood cuttings and is well suitable for year round production of cut flowers in commercial glass houses as a flowering cut rose. This and distinct variety has shown to be uniform and stable in the resulting generations from asexual propagation.

5 Drawing Sheets

BACKGROUND OF THE INVENTION

Figures 1, 2, 3, 4, 5:
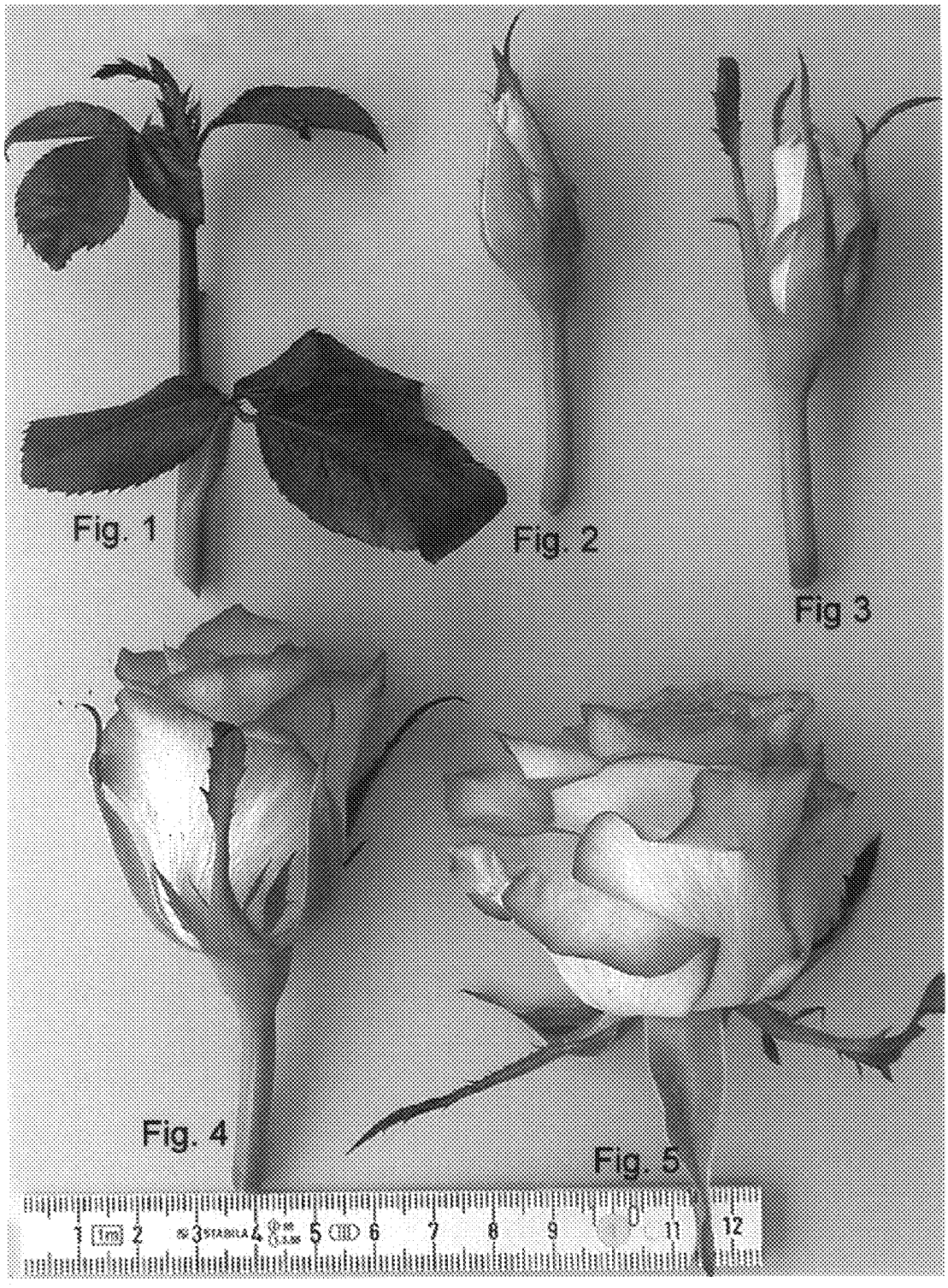

The present invention constitutes a new and distinct variety of Hybrid Tea rose plant, which was developed by artificially pollinating an unnamed seedling(not patent in the U.S.) with an unnamed seedling (not patent in the U.S.). The two parents were crossed in the summer of 1998 and the resulting seed was sown in December 1998, in a controlled glasshouse environment. Out of these seedlings one seedling was selected, as the new variety and named 'KORolesola'. The new rose may be distinguished from its seed parent, an unnamed seedling, by the following combination of characteristics:

1. The unnamed seedling has many thorns on the branches while 'KORolesola' has few thorns.
2. 'KORolesola' has big double flowers, while the unnamed seedling has big single flowers.
3. 'KORolesola' has thick creme-pink colored petals, while the unnamed seedling has dark orange-red petals.

The new variety may distinguished from its pollen parent, an unnamed seedling created by the same inventor, by the following combination of characteristics:

1. The pollen parent has matt foliage while 'KORolesola' has glossy foliage.
2. 'KORolesola' has bigger flowers and foliage as compared to the unnamed seedling.
3. 'KORolesola' has creme-pink colored petals, while the unnamed seedling has creme colored petals.

BRIEF SUMMARY OF THE INVENTION

Initial asexual reproduction of 'KORolesola' by cuttings was first done in Klein Offenseth-Sparrieshoop, Germany. The reproduction was conducted in controlled greenhouse environments.

Have here proven to be stabile by propagation with cuttings in several generations.

'KORolesola' is a high productive Hybrid Tea rose with a vaselife greater than 14 days.

'KORolesola' under conventional greenhouse production (18 degree Celcius nights, and 26 Celcius day's) in Germany will produce 180–260 Stems per year, averaging 60 cm long.

The objective of the hybridization of this rose variety for commercial greenhouse culture was to create a new and distinct variety with:

1. Uniform and abundant flowers with good vaselife.
2. Attractive long lasting foliage and strong growth.
3. Year round flowering under glasshouse conditions.
4. Suitability for production from softwood cuttings.
5. Durable flowers and foliage which make the variety suitable for distribution in the floral industry.

This combination of qualities was not present in previously available commercial cultivars of this type and distinguish 'KORolesola' from all other varieties of which we are aware.

The seeds from hybridization were planted in a controlled environment and evaluations were conducted on the resulting plants. 'KORolesola' was selected by Wilhelm Kordes in their development program in Klein Offenseth-Sparrieshoop, Germany.

BRIEF DESCRIPTIONS OF THE DRAWINGS

The accompanying color illustrations show as true as is reasonably to obtain in color photographs of this type, the typical characteristics of the buds, flowers, leaves, stems of 'KORolesola'. Specifically illustrated in:

Photo Sheet # 1

Young shoot.

FIG. 1. Bud before opening the sepals.

FIG. 2. Bud at the opening the sepals.

FIG. 3. Bud at the opening the petals.

FIG. 4. Flower during course of opening.

FIG. 5. Open flower—plan view.

Photo Sheet # 2

Figures 6, 7, 8, 9:
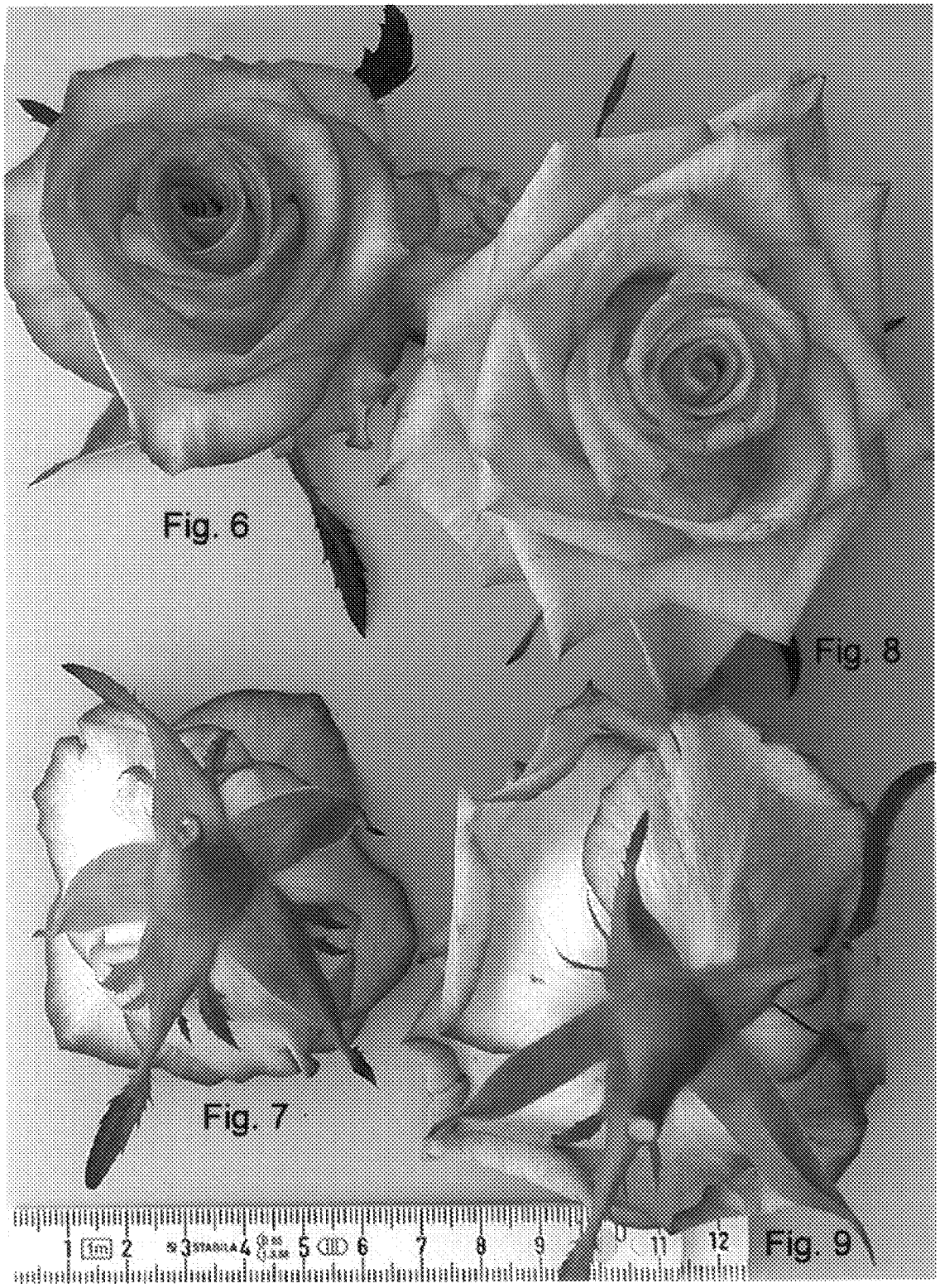

FIG. 6. Open flower —plan view—obverse.

FIG. 7. Open flower—plan view—reverse.

FIG. 8. Fully open flower—plan view—obverse.

FIG. 9. Fully open flower—plan view—reverse.

Photo Sheet # 3

Figures 10, 11, 12, 13, 14:
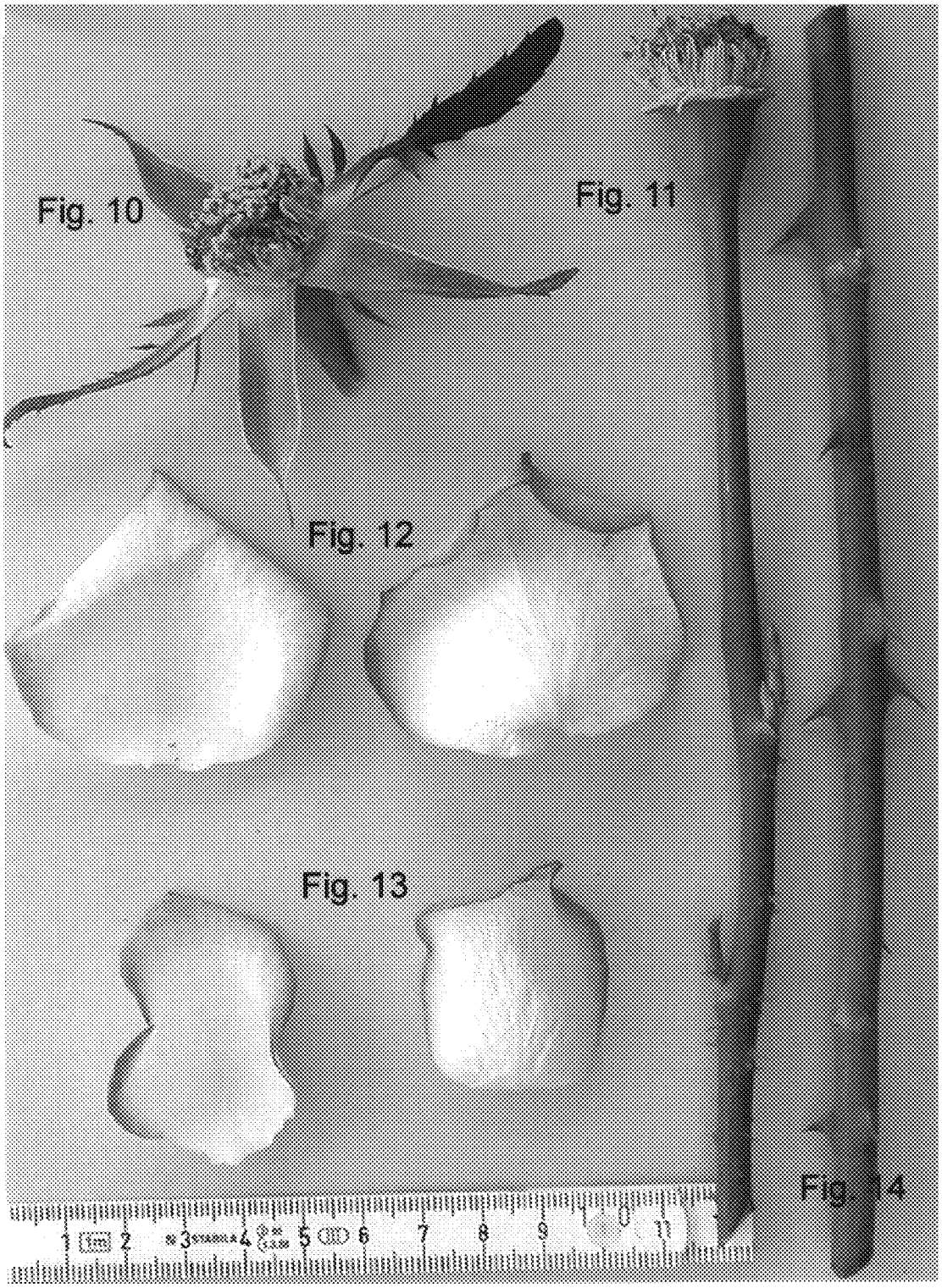

FIG. 10. Receptacle showing stamens and pistils.

FIG. 11. Receptacle showing pistils (stamens removed).

FIG. 12. Flower petals, detached—outer surface.

FIG. 13. Flower petals, detached—inner surface.

FIG. 14. Bare stem exhibiting thorns and flower attachment.

Photo Sheet # 4

Figures 17, 18:
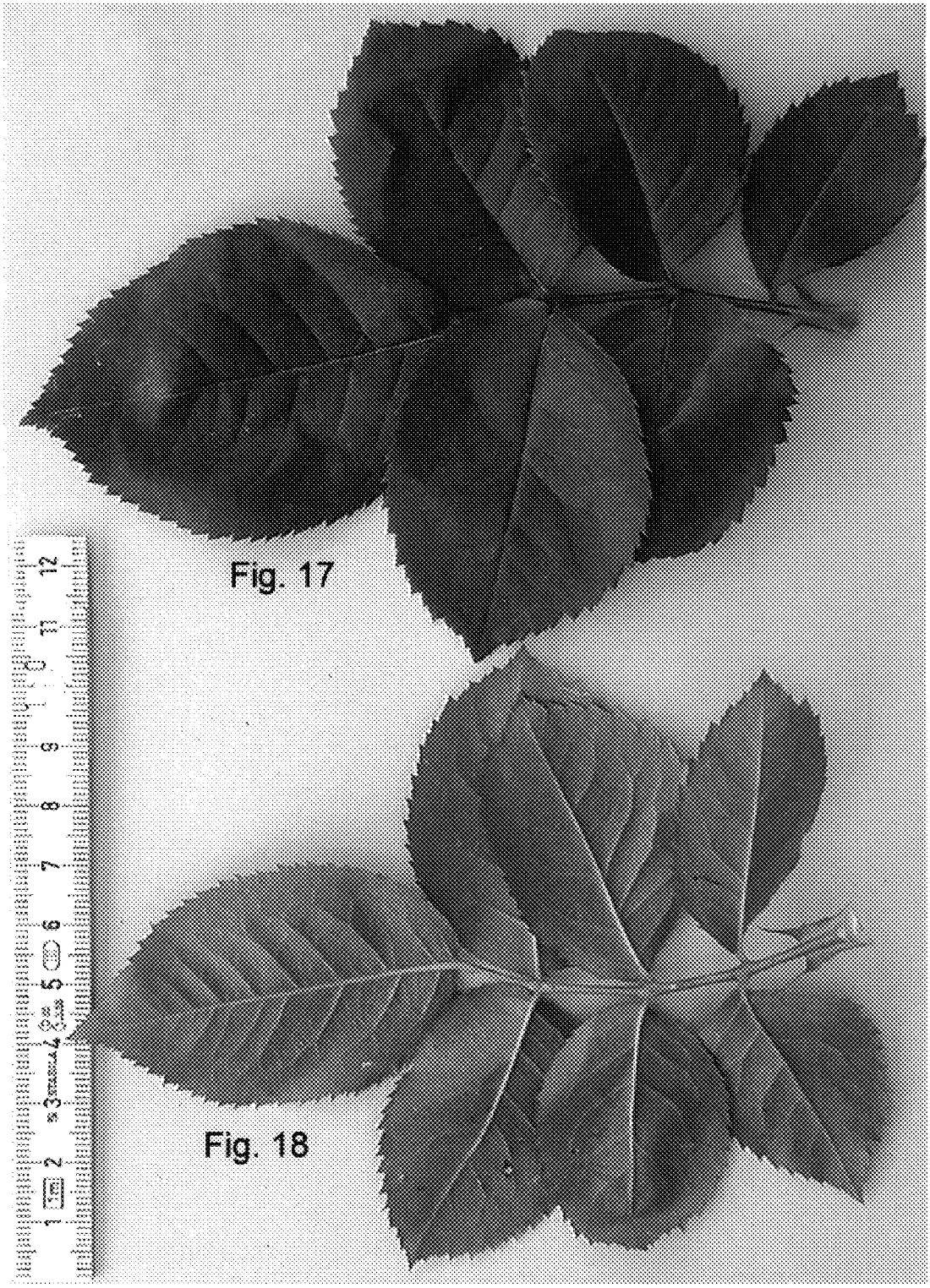

FIG. 17. Five leaflets upper side.

FIG. 18. Five leaflets reverse side.

Photo Sheet # 5

Figures 15, 16:
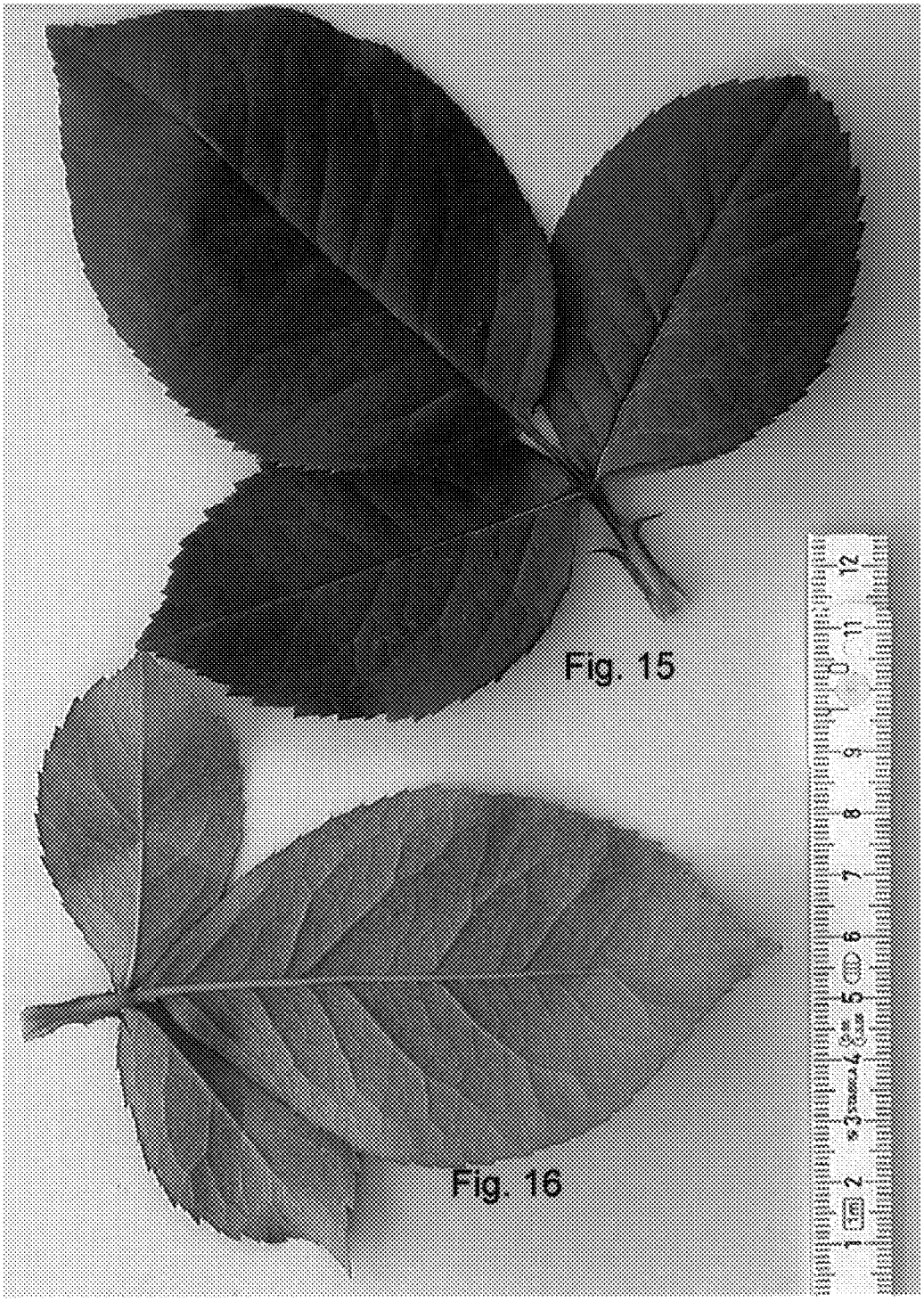

FIG. 15. Three leaflets upper side.

FIG. 16. Three leaflets reverse side.

DETAILED BOTANICAL DESCRIPTION OF THE VARIETY

The following is a detailed description of the Hybrid Tea Rose: *Rosa hybrid* 'KORolesola'.

The following observations, measurements, values and comparisons describe plants grown in glass houses in Klein Offenseth-Sparrieshoop, Germany.

The age of the observed plants where 11 to 13 months after propagation by cuttings, and produced as flowering cut-rose plants.

Color references are made using The Royal Horticultural Society (London, England) Colour Chart, 1995, except where common terms of color are used.

For a comparison, the nearest existing rose variety is 'JACnepal', a rose variety described and illustrated in U.S. Plant Pat. No. 11,691.

Chart 1 details several physical characteristics of 'KORolesola' and 'JACnepal'.

CHART 1

| | 'KORolesola' | 'JACnepal' |
|---|---|---|
| Petal color, Upper surface | White Group 155D Edge: Red-Purple Group 58C | Orange-White Group 159D Edge: Red Group 45D |
| Petal color, Reverse surface | White Group 155D Edge: Red-Purple Group 58C | Orange-White Group 159D Edge: Red Group 45D |
| Petal count | 40–45 | 30–35 |

Parents: Unnamed seedling. Times. Unnamed seedling.

Classification:

*Botanical.*—*Rosa hybrid.*

*Commercial.*—Hybrid Tea.

Plant:

*Plant growth.*—Very vigorous. Grows Strong upright to bushy. Production time is for floral stems is generally 6 to 8 weeks depending on average temperature, light level, and cultural practices.

*Height.*—Plants which were pruned at height of 0.5 meter, produce floral stems having a length of 40 to 90 cm.

Stem:

*Color.*—Young wood: Green Group 137 A, with intonations of Red-Purple Group 59A. Older wood: Green Group 139A.

*Thorns.*—Incidence: Low number of thorns. Size: 7–8 mm. Color: Greyed-Purple Group 183B. Shape: Deep concave, bending downward.

*Surface.*—Young wood: Smooth. Older wood: Smooth.

*Stem diameter.*—5–6 mm.

*Internode length.*—60–70 mm.

*Numbers of internodes.*—8–12.

Plant foliage: Leaves arranged alternately, compound with three to seven leaflets per leaf, generally symmetrical, abundant, and flat in aspect. Stipules at petiole base.

*Quantity of leaves.*—8 to 12 per lateral branch.

*Leaf size.*—Medium 170–180 mm(l). times. 130–135 mm(w).

*Petioles.*—Color: Yellow-Green Group 152A, with intonations of Greyed-Red Group 185A. Margins: entire with few thorns. Length: 20–25 mm Diameter: about 2–3 mm.

*Stipules.*—Size: 10–12 mm. Surface: Smooth. Color: Green Group 139C. Margins: Serrated.

*Rachis.*—Color: Yellow-Green Group 152A, Margins: Margins with prickles. Length: 20 to 25 mm.

*Leaflets.*—Edge: Serrated. Serration: Single. Shape: Ovate with acute apex and obtuse base. Texture: Smooth. Appearance: Glossy. Size: length: 60 to 70 mm. With: 40 to 50 mm. Color: Young foliage: Upper surface: Red-Purple Group 59A. Lower surface: Red-Purple Group 59A. Color: Mature foliage: Upper surface: Green Group 139A. Lower surface: Greyed-Green Group 191B.

Inflorescense:

*Blooming habit.*—Recurrent.

*Number of flowers.*—Generally 1 bud per flowering stem.

*Penduncle.*—Color: Green Group 143A. Texture: Smooth. Length: 70–75 mm. Upright: 0 3–4 mm.

*Receptacle.*—Surface: Smooth, glabrous. Shape: Funnel-shaped. Size: h: 10–12 mm. w: 8–10 mm. Color: Green Group 143A.

*Sepals.*—Quantity: 5. Shape: Narrowly Ovate w. acute tip. Texture: Leathery. Margin: Foliaceous appendages on 2 of the five sepals. Appearance: Dull. Color: Upper surface: Green Group 138C. Reverse surface: Green Group 143D. Petaloids: 1–3 per flower. Size: 1–1,5 cm long and 0,3–07 cm wide. Shape: narrow elliptical. Color: White Group 155 D with intonation of Red-Purple Group 58X.

*Buds.*—Size: 30–35 mm (h) 20–25 mm (w)upon opening. Shape: Cupped. Color: at ¼ opening, White Group 155D.

*Flower.*—Duration. As a cutflower, flowers last from 12 to 16 days. Fragrance. None. Size: 70–75 mm in diameter. Form: Shape of flower when viewed from the side. Up on opening: Cupped to pointed. Open flower: Cupped. Color: Petals, upon opening. Upper surface: White Group 155D, edge colered in Red-Purple Group 58C. Reverse surface: White Group 155D, edge colored in Red-Purple Group 58C. Petals after opening: Upper surface: White Group 155D, edge colered in Red-Purple Group 58C. Reverse surface: White Group 155D, edge colered in Red-Purple Group 58C. General tonality: On Open flower: Third day: White Group 155D, with intonation of Red-Purple Group 58C. Afterwards: White Group 155D, with intonation of Red-Purple Group 58C.

*Petals.*—Petal reflex. Outermost petals reflex backwards at opening. Fully open all petals reflex backwards. Texture. Smooth. Petal edge. Uniform. Petal count. Approximately 40–45 on the average per flower. Petal size. Length 45 mm With: 50 mm. Shape. Outer petals: Round. Inner petals: Ovate.

*Reproductive organs.*—Stamen number: Approximately 80–85 on average per flower. Pollen. Color: Yellow-Green Group 150D. Pollen abundance: Average. Anthers. Size: 1–2 mm Color: Yellow-Orange Group 15C. Shape: Oblong. Filaments. Size: 6–7 mm Color: Yellow-Green Group 150D. Pistils number: Approximately 50–60 on average per flower. Stigmas. Location: Superior in location to anthers Color: Yellow Group 11D. Styles. Color: Red-Purple Group 57B. Length: 3 to 4 mm.

Development:

*Vegetation.*—Dense.

*Blooming.*—Abundant.

*Aptitude to bear fruit.*—Poor.

*Resistance to diseases.*—Above average resistance to mildew and Botrytis under normal growing conditions in Klein Offenseth-Sparrieshoop, Germany.

Hips/seeds has not been observed due to that the plant has never been grown to the stage of seed development, due to the fact, that the variety is developed for producing floral stems only.

Winter hardiness & Drought/heat tolerance: Due to the fact, that this variety is a cutrose plant, developed for producing floral stems only, the plant is not tested for winter hardiness or drought/heat tolerance.

I claim:

1. A new and distinct variety of rose plant of the Hybrid Tea class, substantially as herein illustrated and described as a distinct and novel rose variety due to its abundant creme-pink colored flowers, attractive long lasting foliage, vigorous and upright growth, year round flowering under glasshouse conditions, suitability for production from softwood cuttings, and durable flowers and foliage which make the variety suitable for distribution in the floral industry.

* * * * *